United States Patent [19]

Imbert

[11] Patent Number: 5,282,792
[45] Date of Patent: Feb. 1, 1994

[54] SYRINGE HAVING TWO COMPONENT BARREL

[75] Inventor: Claude Imbert, La Tronche, France

[73] Assignee: Becton, Dickinson and Company, Franklin Lakes, N.J.

[21] Appl. No.: 918,715

[22] Filed: Jul. 21, 1992

[51] Int. Cl.[5] ............................................. A61M 5/00
[52] U.S. Cl. .................................... 604/187; 604/227; 206/571
[58] Field of Search ............... 604/187, 218, 227, 232, 604/199; 206/570, 571, 365

[56] References Cited

U.S. PATENT DOCUMENTS

| | | |
|---|---|---|
| 801,912 | 10/1905 | Rehmann . |
| 1,142,682 | 6/1915 | Dickinson . |
| 1,798,116 | 2/1928 | Brockway . |
| 2,047,512 | 7/1936 | Kauffman ............................. 604/227 |
| 2,678,647 | 5/1954 | Bruger ................................. 604/227 |
| 3,987,940 | 10/1976 | Tischlinger ....................... 604/227 X |
| 4,068,661 | 1/1978 | Hennings ............................. 604/227 |
| 4,112,945 | 9/1978 | Helixon et al. . |
| 4,469,482 | 9/1984 | Lissenburg et al. . |
| 4,792,329 | 12/1988 | Schreuder . |
| 4,840,616 | 6/1989 | Banks ................................. 604/110 |
| 4,878,903 | 11/1989 | Mueller ............................... 604/199 |
| 4,909,788 | 3/1990 | Egdf .................................. 604/187 |

FOREIGN PATENT DOCUMENTS

| | | |
|---|---|---|
| 773091 | 10/1971 | Belgium ............................... 604/227 |
| 20266 | 12/1929 | Netherlands ......................... 604/227 |
| 1479536 | 7/1977 | United Kingdom . |

Primary Examiner—John D. Yasko
Assistant Examiner—Mark O. Polutta
Attorney, Agent, or Firm—Arthur D. Dawson

[57] ABSTRACT

A syringe assembly includes a hollow cylindrically shaped barrel. The external side of the barrel has a first portion at its proximal end, a second portion adjacent the first portion and a third portion adjacent the second portion. The diameter of the second portion is less than the diameter of the first portion resulting in formation of a shoulder at the intersection of the first and second portions. The third portion outside diameter adjacent the second portion is substantially equal to the outside diameter of the second portion and increases to the outside diameter of the barrel. The assembly further includes a finger flange with a first side and a second side and an opening with an inside wall. The flange opening has an annulus positioned within it which has an opening. The annulus has an end attached to the inside wall of the flange opening and an unattached end projecting toward the first side of the flange, and forms an acute angle with the inside wall of the flange opening. The flange is held by the barrel so that the opening of the annulus rests at the second portion and the unattached end of the annulus is positioned adjacent to the shoulder so that a distal force for installing the flange is less than a proximal force for removal of the flange.

17 Claims, 5 Drawing Sheets

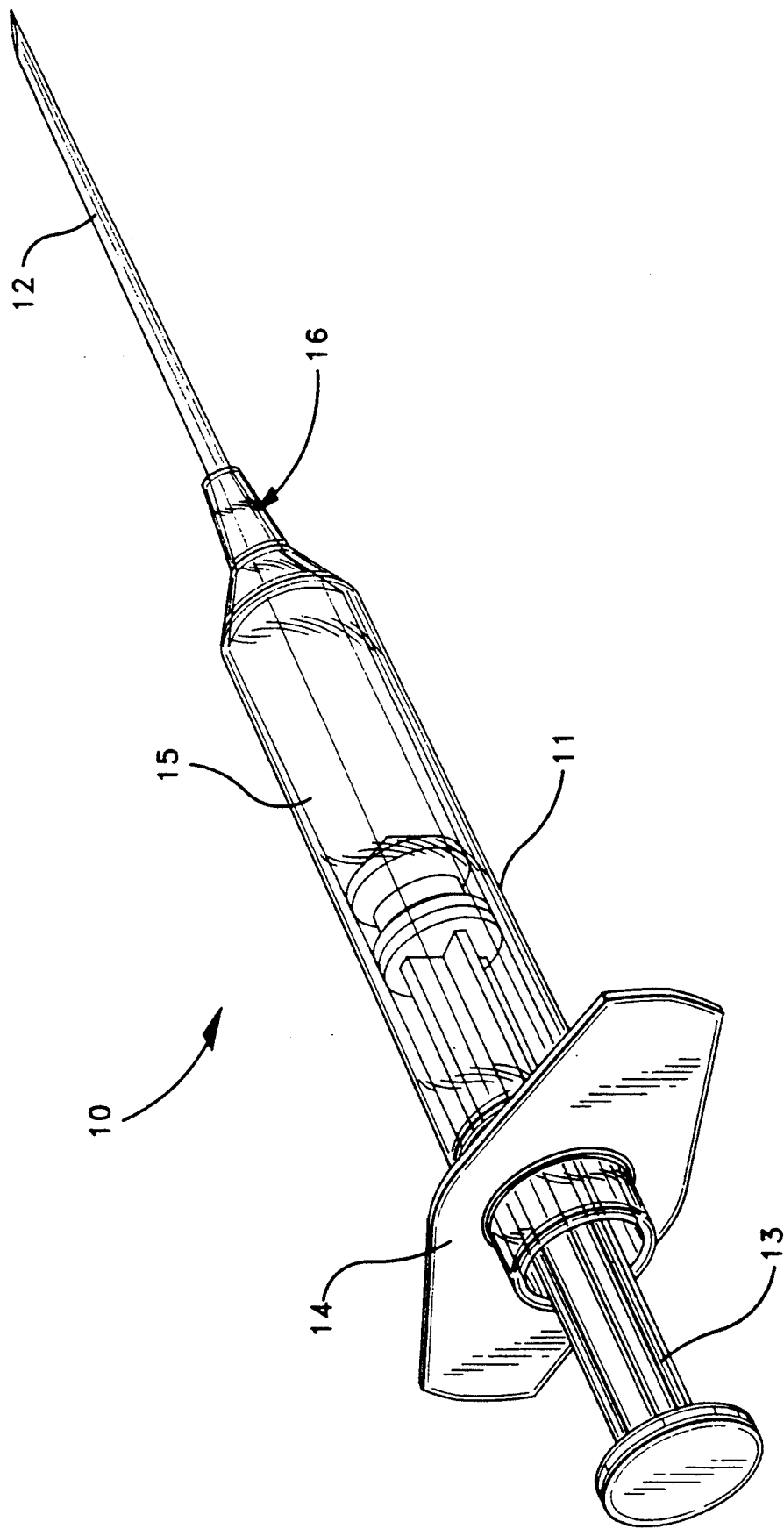

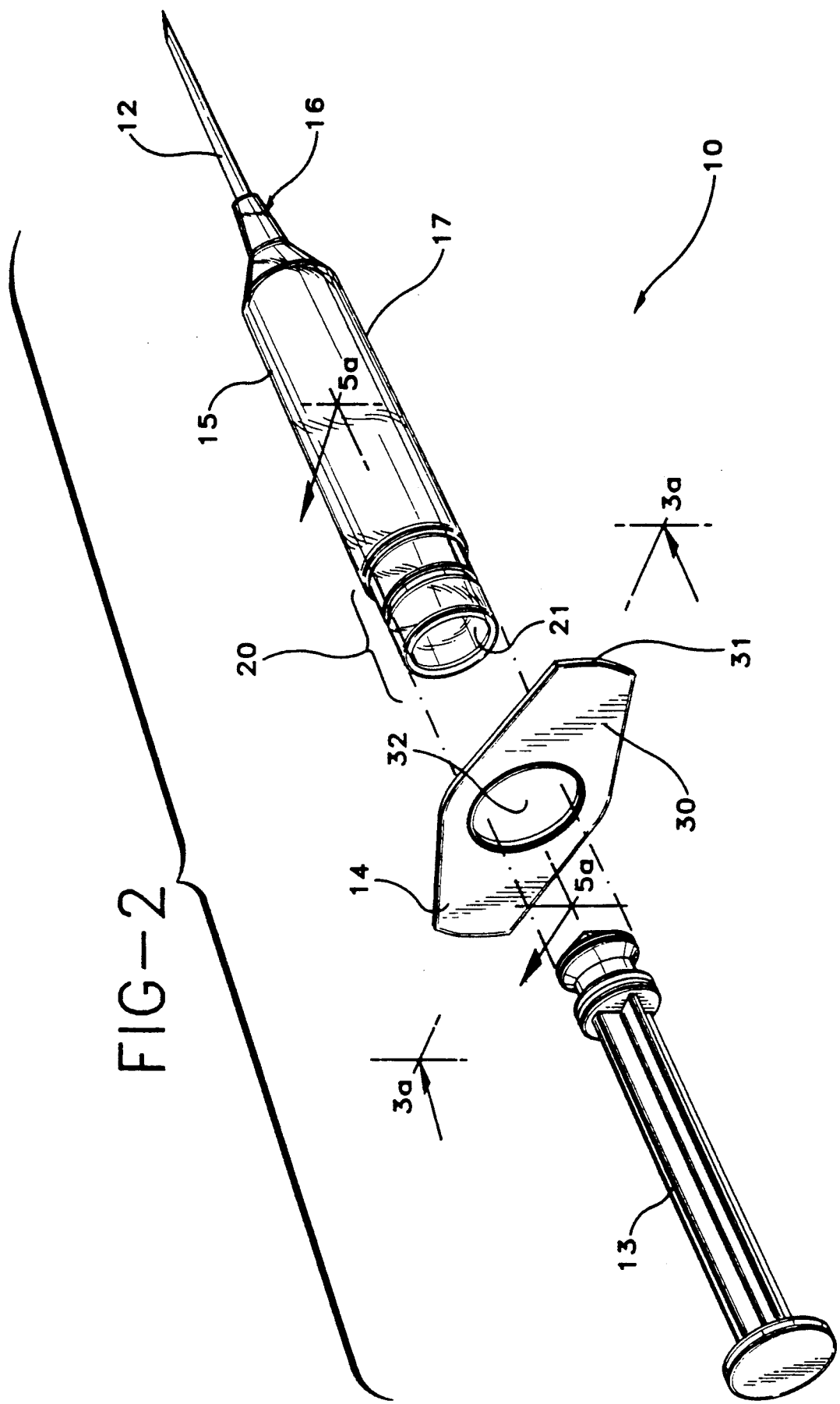

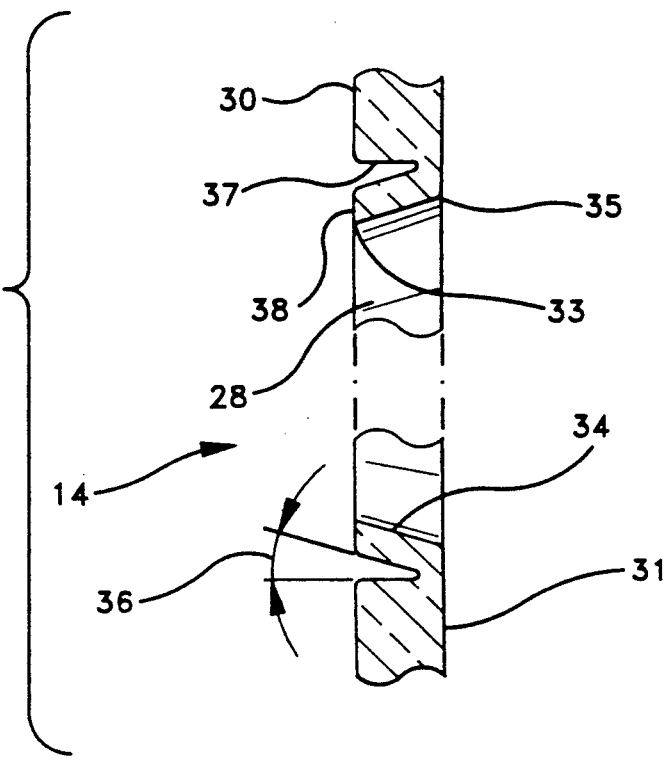
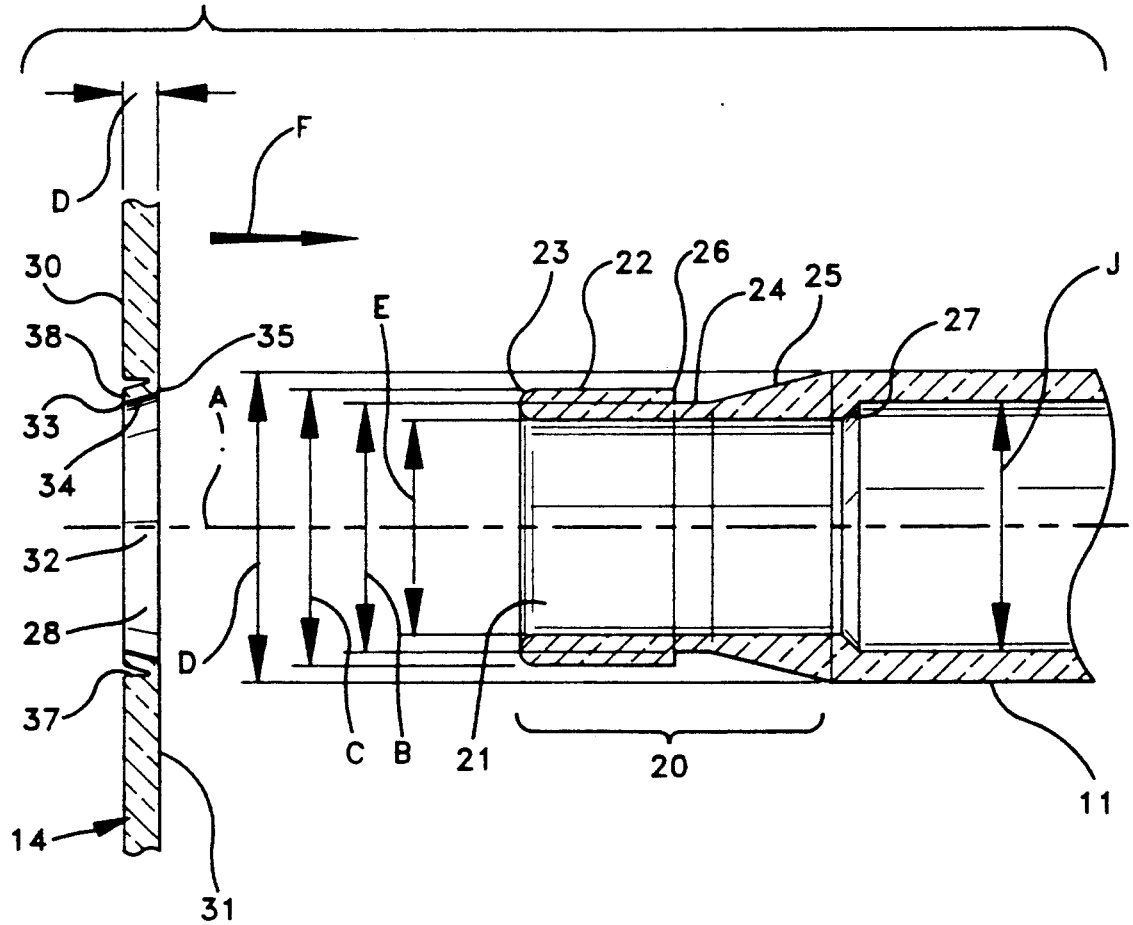

SYRINGE HAVING TWO COMPONENT BARREL

BACKGROUND OF INVENTION

1. Field of the Invention

This invention relates to syringes and more particularly to syringes with a finger flange attached to a barrel.

2. Description of Related Information

Generally speaking, a hypodermic syringe consists of a cylindrical barrel, most commonly made of a thermoplastic material or glass, having a distal end connected to a sharp needle or adapted to be connected to a hypodermic needle assembly, a proximal open end having an external finger flange and internally adapted to receive a resilient stopper.

In most cases, the finger flange is integrally formed with the barrel. The process of integrally forming the flange and the barrel limits the design of the flange, particularly in the case of a glass barrel formed from glass tubing. Further, the need to provide sufficient strength for the flange requires the proximal end of the barrel portion to be more massive than would be required to accommodate only the volume. This additional size may affect the ability of the syringe to be fit into syringe pumps.

In the case of syringes intended for prefilling and subsequent use as a package for a medicament, the presence of a fixed flange constrains the design of the processing and filling apparatus. Further, the presence of a fixed flange may make the barrel more prone to breakage during the processing and filling operations, as well as during handling, preparation and set up for the injection.

Syringes have been in use for many years. Several early designs of syringes have had flanges formed from materials other than glass and subsequently attached to the barrel by clamping, threading or the like. Patents exemplary of these types of devices are described below.

U.S. Pat. No. 801,912 teaches a glass syringe barrel with a proximal rim and a metal finger flange apparently put on from the distal end of the barrel and slid proximally to engage the rim. The metal flange is held against the rim by an internal flat spring compressed against the barrel.

U.S. Pat. No. 1,142,682 teaches a separate flange installed over the distal end of the syringe and slid proximally along the barrel to a proximal rim. The flange includes a spring which serves to hold the collar with the flange against the barrel's proximal rim and also maintains tension against the plunger.

U.S. Pat. No. 1,798,116 teaches a two part finger flange which has a threaded collar containing the flange placed over the distal end of the syringe, then slid upwardly to the proximal end of the syringe. A threaded plug is then inserted into the proximally placed threaded collar on top of a swedging ring and tightened down to hold the flange in position at the proximal end of the barrel.

U.S. Pat. No. 4,112,945 teaches a syringe designed to receive a prefilled cartridge which has threaded cap with radially extending arms to provide finger holds. When the cap is threaded onto the barrel containing the cartridge, the cap serves to retain the cartridge and provide the finger holds.

U.S. Pat. No. 4,469,482 teaches a disposable syringe having a finger grip connected around the barrel according to the "so-called snap-cap principle." This device apparently comprises a planar flange with a central extended collar to fit around and over the proximal end of the syringe. There is no teaching in the specification of the structure of the "so called snap cap," however, FIG. 1, element 16 apparently shows a semicircular projection on the cap in apparent conjugation with a recess on the proximal end of the barrel.

U.S. Pat. No. 4,702,329 teaches a syringe in which the cylindrical body is an ampoule having closures at each end. The proximal closure functions as a plunger stopper after attachment of a plunger rod. A finger grip is mounted on the outside of the ampoule by the "so-called snap cap principle." The '329 patent teaches that the finger grip is preferably manufactured from a slightly resilient but non-deformable material, for example a synthetic. The '329 patent also teaches another embodiment where the finger grip forms are one assembly with the ampoule and may then be formed as a flange like part of the ampoule projecting radially outwards.

British Patent Specification 1,479,536 teaches a finger grip consisting of a tensioning collet which is clamped around the end of the barrel by means of a tensioning sleeve. The patent teaches a finger grip preferably of slightly resilient material for example plastic.

While the art presented above shows several different forms of finger flanges made from metal, glass and plastic, most of the devices taught are multi-component, are applied from the distal end of the barrel and slid to the proximal side. In most of these prior art examples, the assembly of the finger flange requires a complex assembly procedure, a fitting on, a sliding together, a threading and a tightening. In some of the examples a hoop stress or compression is exerted upon the barrel by the flange assembly. Such a stress would be exacerbated by out of-roundness conditions which would tend to concentrate the stress. This stress may lead to distortion or cracking of the barrel, particularly when the barrel is glass.

Thus, in the field of syringes with finger flanges, there still exists a need for a simple to manufacture syringe assembly having as a design feature a finger flange with a higher force for removal than the force for assembly. The higher removal force provides functional utility while the lower installation force provides easy assembly.

SUMMARY OF THE INVENTION

A syringe assembly of the present invention includes a hollow cylindrically shaped barrel with an external side having an outside diameter, an internal side defining a bore and a longitudinal axis. The barrel includes a distal end and a proximal end, the proximal end is open to accept a plunger assembly slidably within the bore. The barrel includes a distal tip with a passageway therethrough in fluid communication with the bore. The external side has a first portion with an outside diameter at the proximal end, a second portion with an outside diameter adjacent the first portion and a third portion with an outside diameter adjacent the second portion. The second portion outside diameter is less than the first portion outside diameter and a shoulder is formed at the intersection of the first portion and the second portion. Adjacent to the second portion, the third portion outside diameter is substantially equal to the second portion. The third portion outside diameter increases to the outside diameter of the barrel at the distal end of the third portion.

The syringe assembly further includes a finger flange with a first side and a second side. The flange has an opening through it with an inside wall. The first side faces the proximal end of the barrel and the second side faces the distal end of the barrel. Positioned within the flange opening is an annulus with an opening. The annulus has an end attached to the inside wall of the flange opening and an unattached end projecting toward the first side of the flange. The annulus forms an acute angle with the inside wall of the flange opening.

The flange is held by the barrel so that the unattached end of the annulus rests at the second portion and is positioned adjacent to the shoulder so that a distal force for moving the flange onto and over the first portion to the second portion is less than a proximal force to move the flange proximally.

A method of manufacturing a syringe assembly with a finger flange includes providing a hollow cylindrically shaped barrel with an external side having an outside diameter, an internal side defining a bore and a longitudinal axis. The barrel includes a distal end and a proximal end, with the proximal end open to accept a plunger assembly slidably with it. The barrel has a tip at the distal end with a passageway through it which is in fluid communication with the bore. The external side has a first portion with an outside diameter at the proximal end, a second portion with an outside diameter is adjacent the first portion. A third portion with an outside diameter is adjacent the second portion. The outside diameter of the second portion is less than the outside diameter of the first portion, and a shoulder is formed at the intersection of the first portion with the second portion. The third portion outside diameter adjacent to the second portion is substantially equal to the second portion outside diameter. The third portion outside diameter increases to the outside diameter of the barrel at the distal end of the third portion.

The method further includes providing a finger flange having first side and a second side, with the flange having an opening with an inside wall through it. The first side of the flange faces the proximal end of the barrel and the second side of the flange faces the distal end of the barrel. The flange opening has an flexible annulus with an opening positioned within it. The annulus has an attached end and an unattached end. The attached end is attached at the inside wall of the flange opening with the unattached end projecting toward the first side forming an acute angle between the annulus and the inside wall of the flange opening.

The method then includes positioning the flange so that the annulus opening is aligned with the first portion of the barrel, and a distal installation force is applied to move the first portion of the barrel through the annulus opening. The installation force is terminated when the unattached end of the annulus rests on the second portion adjacent to the shoulder so that a distal force required to move the flange onto and over the first portion is less than a proximal force to move the flange proximally.

BRIEF DESCRIPTION OF THE DRAWINGS

FIG. 1 is a perspective view of the syringe assembly of the present invention;

FIG. 2 is an exploded perspective view of the syringe assembly of FIG. 1;

FIG. 4 is an enlarged partial cross-section of the flange opening showing the attached annulus; and FIGS. 5a, 5b and 5c are enlarged partial cross-sectional views of the syringe assembly of Fiq. 1 taken alonq the line 5—5, showing the finger flange aligned but unmounted (5a), partially mounted (5b) and fully mounted and engaged (5c).

DETAILED DESCRIPTION OF THE DRAWINGS

Figure 3A:
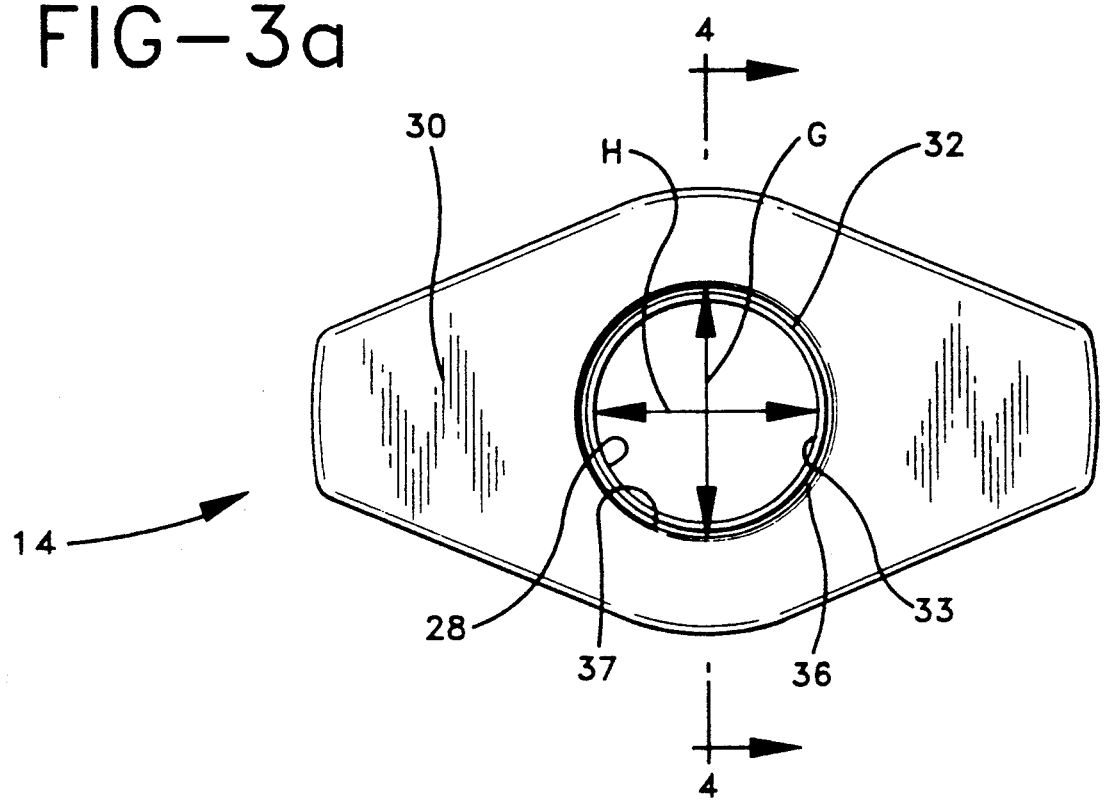
FIG. 3a is a top plan view of the preferred embodiment of the finger flange of the present invention and FIG. 3b is a top plan view of an alternate embodiment of the finger flange of the present invention.

While this invention is satisfied by embodiments in many different forms, there is shown in the drawings and will be herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

As shown in FIGS. 1–5c, an operable syringe assembly 10 comprises a barrel 11, a needle 12, a plunger assembly 13 and a finger flange 14. Barrel 11 includes a cylindrical barrel portion 15 having a longitudinal axis A with needle 12 located at a distal tip 16 having a passage therethrough fluidly communicative with a bore 17 of cylindrical barrel portion 15. Needle 12 has a lumen therethrough in fluid communication with the passage of tip 16. Needle 12 preferably may be fixedly attached to tip 16. Alternatively, needle 12 may be detachable using on of the common hub/tip arrangements for attaching the hub and needle to a syringe tip such as Luer Lok ®, Luer Slip ™ or the like. Barrel 11 further includes a proximal portion 20 having an internal opening 21 to receive plunger assembly 13. Proximal portion 20 includes a first portion 22, preferably including a relieved corner 23, a second portion 24 adjacent the first portion and a third portion 25 adjacent the second portion. Second portion 24 has an outside diameter B which is less than an outside diameter C of first portion 22. Second portion 24 forms a shoulder 26 at the intersection with first portion 22. Shoulder 26 is preferably substantially normal to a longitudinal axis A of barrel 11. Third portion 25 outside diameter is preferably substantially equal to diameter B at its proximal end adjacent second portion 24. Portion 25 outside diameter increases distally to a diameter D which is preferably the diameter of barrel portion 15. Bore 17 has an inside diameter E at proximal portion 20 with an increase to an inside diameter J occurring at the point where third portion 25 becomes cylindrical portion 15 of barrel assembly 11. Preferably an inside diameter transition point 27 functions as an indicator for demarcating the end of useful travel of plunger assembly 13 within cylindrical portion 15. An alternative embodiment wherein diameter J is equal to diameter E with no transition also is possible.

As best illustrated in FIGS. 2, 3a and 4, finger flange 14 comprises a structure having a first side 30, a second side 31 and an opening 32 having a diameter G and an inside wall 37. The first side 30 faces syringe proximal portion 20 and second side 31 faces barrel distal tip 16. An annulus 34 having an opening 28 is positioned within flange opening 32. Annulus 34 has an end 35 attached to inside wall 37 and an unattached end 38 projecting toward first side 30. Annulus 34 forms an acute angle 36 with inside wall 37. A preferred embodiment of flange 14 has end 38 generally coplanar with first side 30, however, end 38 can terminate either above or below a plane defined by surface 30 for specific applications. A preferred placement for attached end 35 is on inside wall 37 adjacent second side 31. The flange can be configured so that the edge at 35 contacts third portion 25 to stabilize the flange and help to prevent movement of the flange relative to the barrel.

Figure 3B:
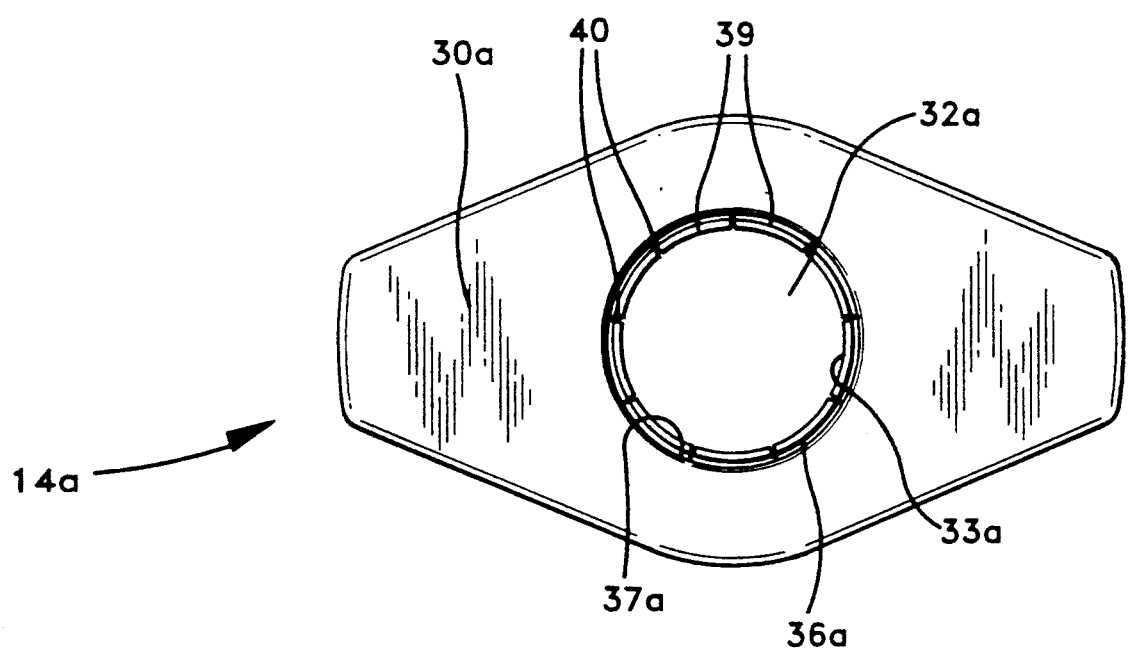

Referring specifically to FIG. 3b, an alternate embodiment of the instant invention is illustrated. In this alternate embodiment, the structure of the finger flange 14 is substantially similar to the embodiment presented in FIGS. 1, 2, 3a and 4. Accordinqly, substantially similar components that perform substantially similar functions will be numbered identically to that component of the embodiment of FIGS. 1, 2, 3a and 4 except that a suffix "a" will be used. In this embodiment, annulus 34a is composed of a plurality of segments 39 alternating with spaces 40 therebetween. Thus, circumference 33a is composed of segments 39 and spaces 40.

Flange 14 is preferably injection molded from a resin selected from the group comprising: polypropylene, polycarbonate, polyamide, polystyrene, polyvinylchloride and acrylonitrile/butadiene/styrene, preferably polypropylene. Barrel 11 can be formed from metal, glass or thermoplastic, with glass being preferred.

Figure 5B:
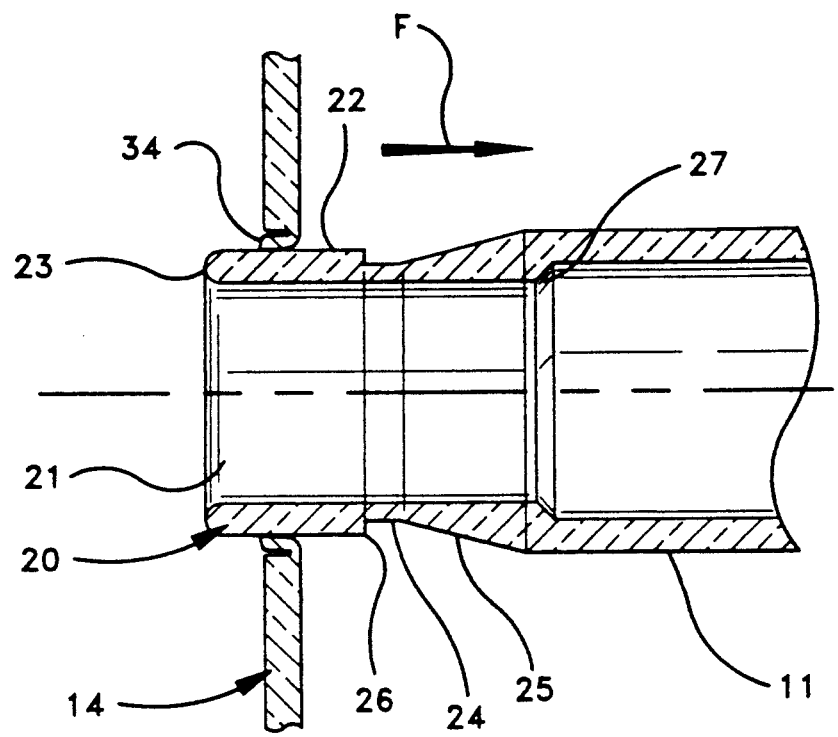
Figure 5C:
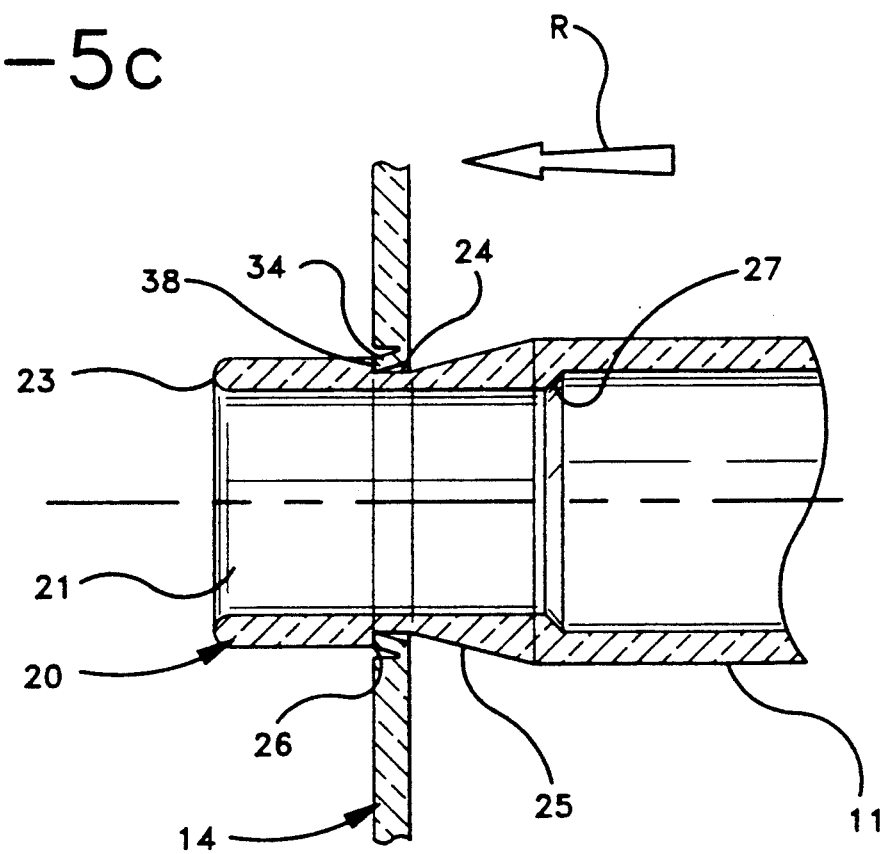

Referring to FIGS. 5a, 5b and 5c, proximal portion 20 of barrel 11 is shown as during assembly with flange 14 in three different positions respectively: 5a) prior to placement; 5b) partially mounted after application of a distal installation force showing annulus 34 deflected on first portion 22; and 5c) fully mounted with unattached edge 38 of annulus 34 at rest at second portion 24 adjacent shoulder 26 at the intersection of first portion 22 and second portion 24. A distal installation force F is applied to cause annulus 34 of flange 14 to deflect and allow flange 14 to move onto first portion 22. When annulus opening 28 is placed over first portion 22, annulus 34 is deflected, reducing angle 36, compliantly enlarging circumference 33 and increasing diameter H. Corner 23 of first portion 22 is preferably relieved by a chamfer or radius to aid in placing opening 28 of annulus 34 onto first portion 22. Fiq. 5c shows unattached end 38 of annulus 34 at rest at in second portion 24 and adjacent shoulder 26 after movement by force F over first portion 22. The force F is then terminated.

As best illustrated in Figs. 3a, 5a, 5b and 5c, diameter H preferably is smaller than diameter B of portion 24, thus providing an interference fit between flange 14 and barrel 11 at portion 24. It should be recognized that the amount of this interference and other dimensional relationships will vary with general dimensional relationships. As the barrel and flange dimensions become larger or smaller, or when other materials are used, one skilled in the art will recognize that the interference relationships may change.

When flange 14 is fully positioned at second portion 24, a proximal removal force R is required to move flange 14 from second portion 24 back to first portion 22 and further to entirely remove it from barrel 11. The design of flange 14 with annulus 34 having opening 28, which rest adjacent shoulder 26 at the intersection of portions 22 and 24 is such that a removal force R is greater than installation force F, thus providing for enhanced functional utility for finger flange 14. Additionally, the several design features of annulus 34 with opening 28 having unattached end 38 resting adjacent shoulder 26 serve to position finger flange 14 upon proximal portion 20 of barrel 11 to resist removal force R. Because of the compliant nature of the plastic resin used to mold flange 14 and the unique design of annulus 34 which has attachment point 35 with angle 36 between sidewall 37 and the annulus, any stresses generated by flange 14 upon proximal portion 20 of barrel 11 are uniformly and compliantly spread over the entire area of second portion 24. Thus problems are avoided associated with the prior art designs having clamping stress and hoop stress which are more sensitive to dimensional variations. Further, the design allows installation force F to be low for easy assembly, while having high removal force R to ensure flange utility when performing a procedure with syringe 10. Flange 14 substantially reduces breakage of a glass barrel 11 by serving as a compliant shock absorber if the syringe is dropped or falls during use.

The syringe assembly may be placed in a microorganisms resistant package formed from materials known to the art and exposed to a sterilizing environment. This sterilization after packaging allows supply and storage of sterile syringe assemblies. Alternatively, the assemblies can be supplied unassembled and nonsterile or sterile to a user who would assemble, fill and sterilize them as required.

An additional benefit of separately manufacturing flange 14 from barrel 11 is the ability to change the external shape of finger flange 14 to meet particular application requirements, such as a special design specifically to mount the syringe in an particular apparatus. Further, barrel 11 can be provided without any finger flange, but having the hereinabove described design of proximal portion 20 of barrel 11 available for removably interlocking with apparatus designed to accept it. Another advantage would be the ability to complete assembly, filling, packaging and sterilization without mounting a flange, the flanges being included separately as a compact addition, thus greatly reducing the cubing space requirements required for a given number of syringes. Since the flanges are easily mounted on the barrel, they could be placed on an already filled barrel immediately after filling or by the ultimate user as required. This ability to be compactly packaged greatly improves the efficiency of sterilization by more completely utilizing the space in the sterilizer.

Thus, the design of syringe assembly 10 having flange 14 provides an advance over the prior art of syringe assembly design.

What is claimed is:

1. A syringe assembly comprising:
a hollow cylindrically shaped barrel including an external side having an outside diameter, an internal side defining a bore and a longitudinal axis, said barrel including a distal end and a proximal end, said proximal end being open to accept a plunger assembly slidably within said bore, said barrel having a tip at said distal end having a passageway therethrough in fluid communication with said bore, said external side having a first portion with an outside diameter at said proximal end, a second portion with an outside diameter adjacent said first portion, and a third portion with an outside diameter adjacent said second portion, said second portion outside diameter being less than said first portion outside diameter, a shoulder formed at the intersection of said first portion and said second portion, said third portion outside diameter adjacent said second portion being substantially equal to said second portion outside diameter, with said third portion outside diameter increasing to said outside diameter of said barrel at the distal end of said third portion and said first portion outside diameter being less than said outside diameter of said barrel at the distal end of the third portion;

a finger flange having a first and a second side and an opening therethrough having an inside wall, said first side facing said proximal end of said barrel and said second side facing said distal end of said barrel, said flange having an annulus with an opening therethrough positioned within said flange opening, said annulus having an attached end and an unattached end, said attached end being attached at said inside wall of said flange opening and said unattached end projecting toward said first side, forming an acute angle between said annulus and said inside wall; and said flange being held by said barrel so that said unattached of said annulus rests at said second portion nd is positioned adjacent said shoulder so that a distal force required to move said flange onto and over said first portion to said second portion and position said unattached end of said annulus adjacent said shoulder is less than a proximal removal force to move said flange proximally.

2. The syringe assembly of claim 1 wherein said annulus opening diameter is smaller than said outer diameter of said second portion of said barrel so that a diametric interference exists between said second portion of said barrel and said annulus opening diameter.

3. The syringe assembly of claim 1 wherein said attached end of said annulus is attached at said inside wall of said flange opening adjacent said second side of said flange.

4. The syringe assembly of claim 1 wherein said shoulder is substantially normal to said longitudinal axis of said barrel.

5. The syringe assembly of claim 1 further including a needle having a lumen therethrough fixedly attached to said tip and in fluid communication with said passageway.

6. The syringe assembly of claim 1 further including a needle having a lumen therethrough detachably mounted on said tip and in fluid communication with said passageway.

7. The syringe assembly of claim 1 wherein said annulus of said finger flange is composed of a plurality of segments arranged circumferentially around said opening.

8. The syringe assembly of claim 1 wherein said finger flange is planar.

9. The syringe assembly of claim 1 wherein said barrel further includes a plunger assembly slidably positioned within said bore.

10. The syringe assembly of claim 1 wherein said barrel is formed from glass.

11. The syringe assembly of claim 1 wherein said finger flange is formed of plastic selected from the group consisting of polypropylene, polyamide, polystyrene, polycarbonate, polyvinylchloride and acylonitrile/butadiene/styrene.

12. A syringe assembly comprising:

a cylindrically shaped barrel including an external side having an outside diameter, an internal side defining a bore and a longitudinal axis, said barrel including a distal end and a proximal end, said proximal end being open to accept a plunger assembly slidably within said bore, said barrel having a tip at said distal end having a passageway therethrough in fluid communication with said bore, said external side having a first portion with an outside diameter at said proximal end, a second portion with an outside diameter adjacent said first portion, and a third portion with an outside diameter adjacent said second side portion, said second portion outside diameter being less than said first portion outside diameter, a shoulder formed at the intersection of said first portion and said second portion, said third portion outside diameter adjacent said second portion being substantially equal to said second portion outside diameter, with said third portion outside diameter increasing to said outside diameter of said barrel at the distal end of said third portion and said first portion outside diameter being less than said outside diameter of said barrel at the distal end of the third portion, said barrel having a plunger assembly slidably positioned within said bore;

a finger flange having a first side and a second side and an opening therethrough having an inside wall, said first side facing said proximal end of said barrel and said second side facing said distal end of said barrel, said flange having an annulus with an opening therethrough positioned within said flange opening, said annulus having an attached end and an unattached end, said attached end being attached at said inside wall of said flange opening and said unattached end projecting toward said first side, forming an acute angle between said annulus and said inside wall;

said flange being held by said barrel so that said unattached end of said annulus rests at said second portion and is positioned adjacent said shoulder so that a distal force required to move said flange onto and over said first portion to said second portion and position said unattached end of said annulus adjacent said shoulder is less than a proximal removal force to move said flange proximally; and said annulus opening diameter is smaller than said outer diameter of said second portion of said barrel so that a diametric interference exists between said second portion of said barrel and said annulus opening diameter.

13. A method of manufacturing a syringe assembly with a finger flange comprising:

providing a cylindrical shaped barrel including an external side having an outside diameter, an internal side defining a bore and a longitudinal axis, said barrel including a distal end and a proximal end, said proximal end being open to accept a plunger assembly slidably within said bore, said barrel having a tip at said distal end having a passageway therethrough in fluid communication with said bore, said external side having a first portion with an outside diameter at said proximal end, a second portion with an outside diameter adjacent said first portion, and a third portion with an outside diameter adjacent said second portion, said second portion outside diameter being less than said first portion outside diameter, a shoulder formed at the intersection of said first portion and said second portion, said third portion outside diameter adjacent said second portion being substantially equal to said second portion outside diameter, with said third portion outside diameter increasing to said outside diameter of said barrel at the distal end of said third portion and said first portion outside diameter being less than said outside diameter of said barrel at the distant end of the third portion;

providing a finger flange having a first side and a second side and an opening therethrough having an inside wall, said first side facing said proximal end of aid barrel and said second side facing said distal end of said barrel, said flange having an annulus with an opening therethrough positioned within said flange opening said annulus having an attached end and an unattached end, said attached end being attached at said inside wall of said flange opening and said unattached end projecting toward said first side, forming an acute angle between said annulus and said inside wall;

positioning said flange so that said opening of said annulus is aligned with said first portion;

applying a distal installation force to said flange so that said first portion passes through said opening of said annulus and said unattached end of said annulus rests adjacent said shoulder; and terminating said installation force when said annulus is positioned adjacent said shoulder.

14. The method for manufacturing a syringe assembly of claim 13, further comprising:

providing a detachable needle having a lumen therethrough; and mounting detachably said needle on said distal tip with said lumen in fluid communication with said passageway.

15. The method for manufacturing a syringe assembly of claim 13, further comprising:

providing a needle having a lumen therethrough; and mounting fixedly said needle on said distal tip with said lumen in fluid communication with said passageway.

16. The method of manufacturing the syringe assembly of claim 13 further comprising:

forming a microorganism resistant package from packaging materials resistant to microorganisms;

placing said syringe assembly in said microorganism resistant package;

sealing said package;

placing said package in a sterilizing environment capable of sterilizing said syringe assembly in said package;

exposing said package to said sterilizing environment; and removing said package from said sterilizing environment.

17. The method of manufacturing a syringe assembly of claim 13 wherein said flange is planar.

* * * * *